US00PP09529P

United States Patent [19]

Zaiger et al.

[11] Patent Number: Plant 9,529

[45] Date of Patent: Apr. 30, 1996

[54] PEACH TREE 'SUMMER ZEE'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 415,849

[22] Filed: Apr. 3, 1995

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

Our new development is a distinct variety of peach tree whose novelty consists of the following unique combination of features that are outstanding in a new variety:

1. Fruit with firm flesh having good handling, storage and shipping quality.
2. Heavy and regular production.
3. Large size fruit throughout the tree.
4. Fruit with a high degree of attractive red skin color.
5. Fruit with good flavor and eating quality.
6. Vigorous upright growth.

1 Drawing Sheet

ORIGIN OF THE VARIETY

The new and distinct variety of peach tree was originated by us in our experimental orchard located near Modesto, Calif., as a first generation cross between 'Sweet Gem' Peach (U.S. Plant Pat. No. 7,952) and 'Zee Lady' Peach (U.S. Plant Pat. No. 5,832). We grew and maintained a large group of these first generation seedlings under close and careful observation, during which time we recognized the outstanding fruit characteristics described above and selected the present variety for asexual reproduction and commercialization.

ASEXUAL REPRODUCTION OF THE VARIETY

The present new variety of peach tree was asexually propagated by budding, as performed by us in our experimental orchard located near Modesto, Calif., which shows that all said characteristics run true to the original tree and are established and transmitted through succeeding propagations.

SUMMARY OF THE VARIETY

The present new variety is of large size, vigorous, upright growth and is a productive and regular bearer of large, firm, yellow flesh, freestone fruit with good flavor and eating quality. The fruit is further characterized by holding firm on the tree 7 to 8 days after maturity (shipping ripe), having good storage and shipping quality with a high degree of attractive red skin color. In comparison to its pollen parent 'Zee Lady' Peach (U.S. Plant Pat. No. 5,832), the new variety is approximately 4 weeks earlier in maturity and in comparison to the female parent 'Sweet Gem' Peach (U.S. Plant Pat. No. 7,952), the new variety is approximately 3 weeks later in maturity.

DESCRIPTION OF THE PHOTOGRAPHS

The accompanying photographic illustrations show typical specimens of the foliage and fruit of the present new variety. The upper and lower surface of the leaves are shown, as are the fruit specimens showing the exterior and a sectional view of a fruit divided in the suture plane to show flesh coloration, pit cavity and a stone remaining in place. The photographs were taken shortly after being picked at maturity (shipping ripe) and the colors are as nearly true as reasonably possible in a color representation of this type.

DESCRIPTION OF THE VARIETY

The following is a detailed botanical description of the flowers, foliage and fruit, as based on observations of the specimens grown near Modesto, Calif., with color terminology (except those in common terms) in accordance with *Reinhold Color Atlas* by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Brown to coffee brown (5-E-7) to (5-E-8).

Branches:
- *Size.*—Medium.
- *Texture.*—Medium rough.
- *Lenticels.*—Numerous. Large in size.
- *Color.*—Light brown to brown. Varies with age of growth.

Leaves:
- *Size.*—Large. Average length 7½". Average width 1½".
- *Form.*—Lanceolate — pointed.
- *Texture.*—Smooth.
- *Margin.*—Crenate.
- *Petiole.*—Medium length. Medium thickness.
- *Glands.*—Reniform. Number varies from 2 to 6. Average number 3. Located on lower portion of the leaf blade and upper portion of petiole.
- *Color.*—Upper surface — green to dark green (30-F-5) to (30-F-6). Lower surface — dull green to green (30-E-4) to (30-E-5).

Flower buds:
- *Size.*—Medium.
- *Form.*—Plump.
- *Pubescence.*—Pubescent.

Flowers:
- *Size.*—Medium, non-showy.
- *Blooming period.*—Mar. 4, 1994 to Mar. 10, 1994. Varies slightly with climatic conditions.
- *Pollen.*—Present — self fertile.
- *Color.*—Pink.

Fruit:
- *Maturity when described.*—Firm ripe.
- *Date of first picking.*—Jul. 1, 1994.

*Date of last picking.*—Jul. 8, 1994.

*Size.*—Large. Comparatively uniform. Average diameter axially 3". Average transversely in suture plane 3".

*Form.*—Nearly globose, slightly flattened at stem end.

*Suture.*—Shallow — extends from base to apex.

*Ventral surface.*—Usually rounded, some fruit very slightly lipped.

*Cavity.*—Rounded to slightly elongated in suture plane. Average depth — ½". Average breadth — 1".

*Base.*—Retuse.

*Apex.*—Usually round, varies from slight depression to slight pistil point.

Flesh:

*Ripens.*—Evenly.

*Texture.*—Firm.

*Fiber.*—Few — tender.

*Juice.*—Moderate.

*Flavor.*—Good, mild, good balance between sugar and acid.

*Eating quality.*—Good.

*Amygdalin.*—Undetected.

*Aroma.*—Moderate.

*Color.*—Varies from yellow to golden yellow (4-A-5) to (4-A-6).

Skin:

*Thickness.*—Medium.

*Texture.*—Medium — tenacious to flesh.

*Tendency to crack.*—None.

*Down.*—Moderate amount. Short in length.

*Color.*—Yellow ground color (4-A-6) to (4-A-7). Overspread with red (9-C-8) to (9-D-8).

Stone:

*Type.*—Freestone.

*Size.*—Large. Average length 1½". Average width 1". Average thickness ¾".

*Form.*—Ovoid.

*Base.*—Usually rounded — varies from round to straight.

*Apex.*—Acuminate.

*Sides.*—Equal to unequal.

*Surface.*—Irregularly furrowed toward apex, pitted throughout, heavier toward base. Pits vary from round to elongated.

*Ridges.*—Rounded.

*Tendency to split.*—Very slight.

*Color.*—Brownish red to reddish brown (8-D-6) to (8-D-8).

Use: Dessert.

*Market.*—Local and long distance.

Keeping quality: Good.

Shipping quality: Good.

The new and distinct variety of peach tree, its flowers, foliage and fruit, may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous upright growth and by being a productive and regular bearer of large, firm, yellow flesh, freestone fruit with good flavor and eating quality; the fruit is further characterized by having good handling and shipping quality, holding firm on the tree 7 to 8 days after maturity (shipping ripe), having an attractive red skin color and in comparison to its pollen parent 'Zee Lady' Peach (U.S. Plant Pat. No. 5,832), the new variety is approximately 4 weeks earlier in maturity.

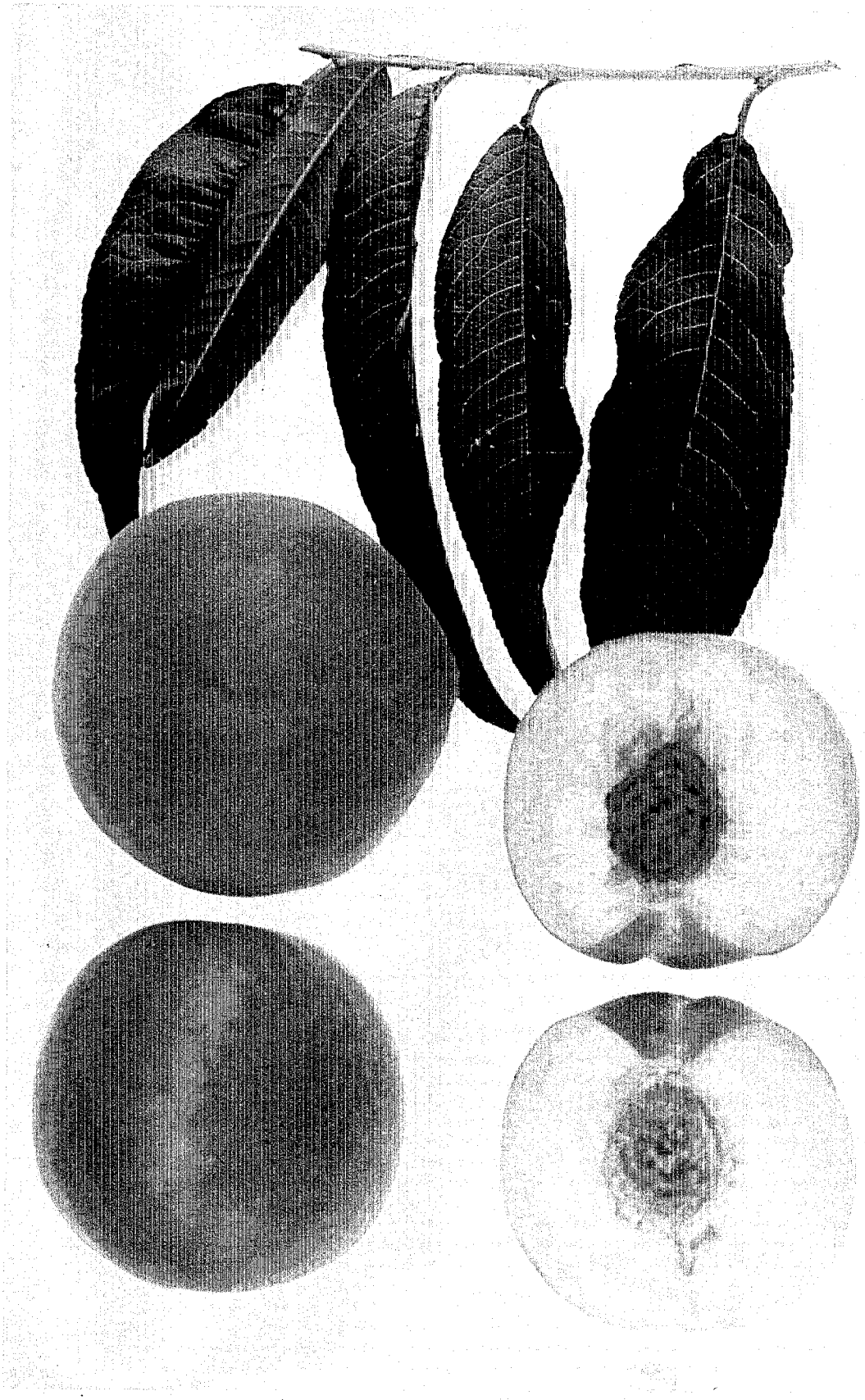

* * * * *